(12) United States Patent
Anderson et al.

(10) Patent No.: US 7,708,743 B2
(45) Date of Patent: May 4, 2010

(54) APPARATUS AND METHOD FOR POSITIONING AN IMPLANT DURING SURGERY

(75) Inventors: Kent Anderson, Memphis, TN (US); Robert H. Dyer, Bartlett, TN (US)

(73) Assignee: Warsaw Orthopedic, Inc.

( * ) Notice: Subject to any disclaimer, the term of this patent is extended or adjusted under 35 U.S.C. 154(b) by 1317 days.

(21) Appl. No.: 11/118,558

(22) Filed: Apr. 29, 2005

(65) Prior Publication Data

US 2006/0253120 A1    Nov. 9, 2006

(51) Int. Cl.
*A61B 17/00* (2006.01)

(52) U.S. Cl. ............................................. 606/99; 606/1

(58) Field of Classification Search ............ 606/1, 606/91, 99, 104; 81/447, 448; 623/17.11–17.16
See application file for complete search history.

(56) References Cited

U.S. PATENT DOCUMENTS

| | | | |
|---|---|---|---|
| 2,802,635 A * | 8/1957 | Engelbart | 254/1 |
| 3,055,676 A * | 9/1962 | McCord | 280/124.136 |
| 4,045,808 A * | 8/1977 | King | 396/155 |
| 4,065,941 A * | 1/1978 | Aoki | 464/115 |
| 4,438,769 A | 3/1984 | Pratt et al. | |
| 4,997,432 A | 3/1991 | Keller | |
| 5,015,247 A | 5/1991 | Michelson | |
| 5,346,115 A | 9/1994 | Perouse et al. | |
| 5,352,219 A | 10/1994 | Reddy | |
| 5,395,391 A | 3/1995 | Essig et al. | |
| 5,441,059 A | 8/1995 | Dannan | |
| 5,452,733 A | 9/1995 | Sterman et al. | |
| 5,454,814 A | 10/1995 | Comte | |
| 5,458,608 A | 10/1995 | Wortrich | |
| 5,464,447 A | 11/1995 | Fogarty et al. | |
| 5,496,323 A * | 3/1996 | Dye | 606/79 |
| 5,613,937 A | 3/1997 | Garrison et al. | |
| 5,618,287 A | 4/1997 | Fogarty et al. | |
| 5,688,276 A | 11/1997 | Shaffer | |
| 5,690,648 A | 11/1997 | Fogarty et al. | |
| 5,735,842 A | 4/1998 | Krueger et al. | |
| 5,772,661 A | 6/1998 | Michelson | |
| 5,788,713 A | 8/1998 | Dubach et al. | |

(Continued)

FOREIGN PATENT DOCUMENTS

WO    WO 02/17823    3/2002

(Continued)

*Primary Examiner*—Henry M Johnson, III
*Assistant Examiner*—Lynsey Crandall

(57) ABSTRACT

An apparatus is provided to hold and orient an implant during a medical procedure and includes an elongated member having an upper member and a lower member with a formed end. A biasing member is operatively positioned between the upper member and lower member and supplies a biasing force to the lower member. A ball joint is provided that includes a ball, and the ball joint accepts the formed end of the lower member. A biasing force is provided by the biasing member to cause the formed end of the lower member to contact the ball. A translation mechanism is used to move the upper member in a first linear direction toward the lower member to cause the formed end of the lower member to lock the ball of the ball joint and, thus, lock the ball joint and orient the ball of the ball joint in a desired position.

23 Claims, 8 Drawing Sheets

U.S. PATENT DOCUMENTS

| | | |
|---|---|---|
| 5,947,970 A | 9/1999 | Schmelzeisen et al. |
| 5,957,927 A | 9/1999 | Magee et al. |
| 6,036,692 A | 3/2000 | Burel et al. |
| 6,113,605 A | 9/2000 | Storer |
| 6,156,037 A | 12/2000 | LeHuec et al. |
| 6,159,200 A | 12/2000 | Verdura et al. |
| 6,165,184 A | 12/2000 | Verdura et al. |
| 6,325,805 B1 | 12/2001 | Ogilvie et al. |
| 6,406,480 B1 | 6/2002 | Beyar et al. |
| 6,428,541 B1 | 8/2002 | Boyd et al. |
| 6,447,512 B1 | 9/2002 | Landry et al. |
| 6,451,054 B1 | 9/2002 | Stevens |
| 6,530,926 B1 | 3/2003 | Davison |
| 7,056,321 B2 | 6/2006 | Pagliuca et al. |
| 2001/0021853 A1 | 9/2001 | Heckele et al. |
| 2002/0045904 A1 | 4/2002 | Fuss et al. |
| 2002/0091390 A1 | 7/2002 | Michelson |
| 2002/0106163 A1* | 8/2002 | Cairns .......................... 385/60 |
| 2003/0208203 A1 | 11/2003 | Lim et al. |
| 2005/0113832 A1 | 5/2005 | Molz, IV et al. |
| 2005/0228400 A1* | 10/2005 | Chao et al. ................... 606/104 |
| 2007/0233087 A1* | 10/2007 | Schlapfer ..................... 606/61 |

FOREIGN PATENT DOCUMENTS

| | | |
|---|---|---|
| WO | WO 03/026513 | 4/2003 |

* cited by examiner

APPARATUS AND METHOD FOR POSITIONING AN IMPLANT DURING SURGERY

BACKGROUND OF THE INVENTION

The present invention relates generally to a medical instrument and method used for positioning an implant during surgery, and more specifically to an articulating implant holder that is adapted to hold, position and orient an implant during surgery and a method for use thereof.

Many medical procedures require precise and accurate positioning of a medical implant before and during surgical implantation of the implant into a patient. As such, during medical procedures, medical personnel, such as surgeons, doctors, surgical assistants and other operating room staff, are interested in using instrumentation that allows for accurate and easy positioning of the implant during surgery. Many conventional medical instruments, such as, implant holders, have been proven to be effective in holding and positioning implants during surgical procedures. However, there is a desire for articulating medical instrumentation used for holding and positioning an implant during a medical procedure. Further, the articulating medical instrumentation should be designed to attain the greatest amount of precision and clamping force while also being simple to operate.

As mentioned above, medical personnel desire new and novel instrumentation to more efficiently hold and position an implant during surgical procedures or to hold or orient the implant relative to the medical instrument to improve visibility or access to the implant. This desire becomes more apparent as surgical procedures move toward minimally invasive surgical techniques where the surgical site has a limited amount of space for the medical personnel to maneuver or operate. Further, new and novel instrumentation becomes even more advantageous in medical procedures, such as, spinal surgery where precisely locating the implant becomes even more important. In these applications, instrumentation having a low profile and/or shape is highly desired. Such low profile and/or shaped instrumentation can easily be maneuvered during surgical techniques that use small surgical openings, such as, minimally invasive surgical techniques.

Precision and maneuverability are also key factors with articulating medical instrumentation that is used to hold and position implants during surgical techniques. There is a desire for a medical instrument that has a more natural and robust movement. Also, there is a desire for a medical instrument where medical personnel can easily position and orient the implant from a distance rather having to physically touch the implant in order to place the implant in a desired position or orientation. In this regard, a medical instrument is further desired where a user can orient or position the implant using only one or two hands rather than having to rely on other medical personnel to assist in orienting the implant. Additionally, it is desired to have a medical instrument where the implant can be easily oriented or positioned in specifically desired positions that are more frequently used in a particular surgical procedure.

Therefore, there is a desire in the industry to provide medical instrumentation and methods for easily orienting and holding a surgical implant during medical procedures. There is, further, a desire for medical instrumentation and method that can easily be maneuvered into small surgical sites and precisely maneuvered near vital internal tissue, organs, blood vessels or nerves. Also, there is a desire for medical instrumentation having a profile and/or shape that prevents the exertion of undesirable forces in or around an implantation area of a surgical site.

BRIEF SUMMARY OF THE INVENTION

In one embodiment, an apparatus is provided to hold and orient an implant during a medical procedure. The apparatus comprises a housing having a first end and a second end. An elongated member that is disposed within the housing. The elongated member also includes an upper member and a lower member. In addition, the lower member has a formed end that is positioned proximate to the second end of the housing. A biasing member is provided that is operatively positioned between the upper member and the lower member. The biasing member has been adapted to supply a biasing force to at least the lower member. A ball joint is provided and includes a ball. The ball joint is positioned at the second end of the housing. The biasing force causes the formed end of the lower member to contact the ball. A mounting portion is connected to the ball and is releasably attached to the implant. A translation mechanism is operatively associated with the first end of the housing and the upper member. The translation mechanism is adapted to move the upper member in at least a first linear direction toward the lower member causing the formed end of the lower member to lock the ball of the ball joint and whereby lock the ball joint and orient the implant in at least a first desired position.

In another embodiment, an apparatus for holding and orienting an implant during a medical procedure is provided. The apparatus comprises an elongated member having an upper member and a lower member. The lower member includes a formed end. A biasing member is operatively positioned between the upper member and the lower member. The biasing member is adapted to supply a biasing force to at least the lower member. A ball joint is provided that includes a ball. The ball joint includes a ball joint housing that houses the ball and is positioned and adapted to accept the formed end of the lower member. A biasing force is provided by the biasing member to cause the formed end of the lower member to contact the ball. A translation mechanism is adapted to move the upper member in at least a first linear direction toward the lower member causing the formed end of the lower member to lock the ball of the ball joint and whereby locking the ball joint and orienting the ball of the ball joint in at least a first desired position.

In yet another embodiment, a surgical method is provided that includes providing a medical instrument. The medical instrument comprises an elongated member having an upper member and a lower member. The lower member includes a formed end. A biasing member is operatively positioned between the upper member and the lower member. The biasing member is adapted to supply a biasing force to at least the lower member. A ball joint is provided that includes a ball. The ball joint is positioned and adapted to accept the formed end of the lower member. A biasing force is provided by the biasing member to cause the formed end of the lower member to contact the ball. A translation mechanism is adapted to move the upper member in at least a first linear direction toward the lower member causing the formed end of the lower member to lock the ball of the ball joint and whereby locking the ball joint and orienting the ball of the ball joint in at least a first desired position. An implant is attached to the medical instrument. Access is provided to an implantation area of a surgical site in a patient. The implant is oriented and locked to the medical instrument in at least one the first desired portion. The medical instrument is inserted into the surgical site in the patient. The medical instrument is positioned in the surgical site whereby the implant is positioned to the implantation area. The implant is attached to the patient at the implantation area. The implant is detached from the medical instrument. The medical instrument is removed from the surgical site of the patient.

DETAILED DESCRIPTION OF THE INVENTION

Figure 1:
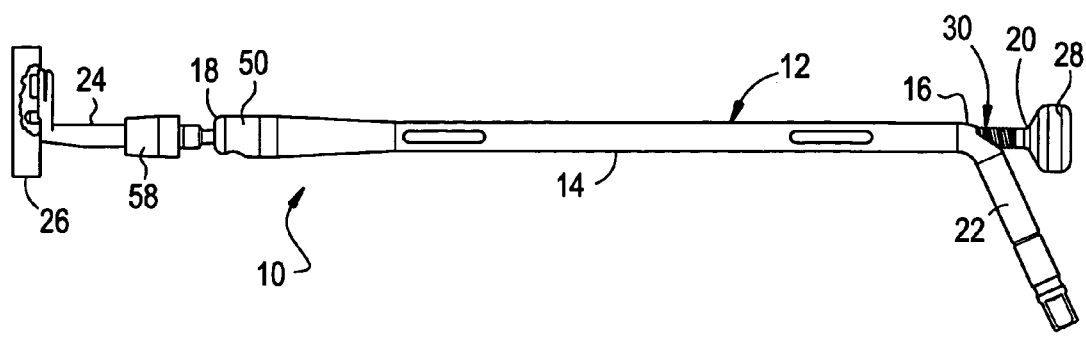
FIG. 1 is a side view of one embodiment of a medical instrument.

For the purpose of promoting an understanding of the principles of the invention, reference will be made to the embodiments illustrated in the drawings and specific language will be used to describe the same. It will nevertheless be understood that no limitation of the scope of the invention is hereby intended nor should be construed. Any such alterations and further modifications in the illustrated devices and described methods, and any such further applications of the principles of the invention as illustrated herein are contemplated as would normally occur to one skilled in the art to which the invention relates.

As shown in FIG. 1, one embodiment of a medical instrument 10 includes an articulating implant holder 12. In this embodiment, the articulating implant holder 12 has a low profile and shape to be easily and accurately positioned and maneuvered during medical procedures, such as, surgery. It should be appreciated that the articulating implant holder 12 can be used in various surgical procedures, such as, spinal surgical procedures. More particularly, the low profile and shape of the articulating implant holder 12 allows for easy, robust and more natural-feeling maneuverability during minimally invasive surgical techniques as well as during open or mini-open surgical techniques. Further, the articulating implant holder 12 has been designed to attain the greatest amount of precision and clamping force while also being simple to operate for medical personnel, such as, operating room staff, assistants, technicians, nurses, doctors and surgeons. Also, the articulating implant holder 12 can be used to orient an implant 26 from a distance, and, if desired, the articulating implant holder 12 can be positioned or oriented without a user having to physically touch the implant 26 after the implant 26 has been mounted to the articulating implant holder 12. Further, in one embodiment, a user can orient or position an implant 26 relative to the articulating implant holder 12 using one or two hands and without having to rely on other medical personnel to assist in the positioning and/or orientation of the implant 26 relative to the articulating implant holder 12. In addition, the articulating implant holder 12 includes features that allow the implant 26 to be easily positioned to more frequently used and/or desired orientations. Also, the medical instrument 10 can be oriented relative to the implant 26 to improve the visibility or access to the implant 26 during a medical procedure, such as, surgery.

Figure 8:
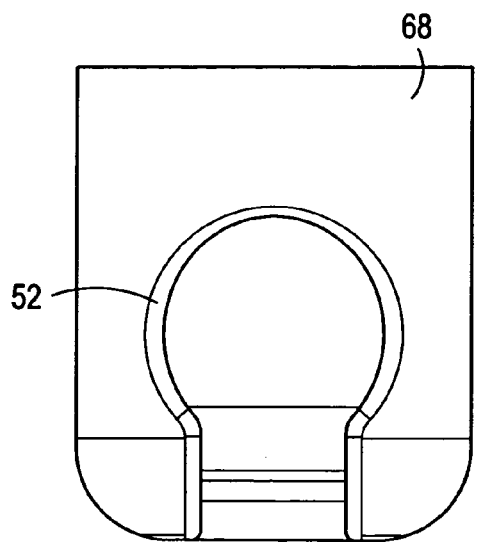
FIG. 8 is a front view of one embodiment of a ball joint housing.
Figure 9:
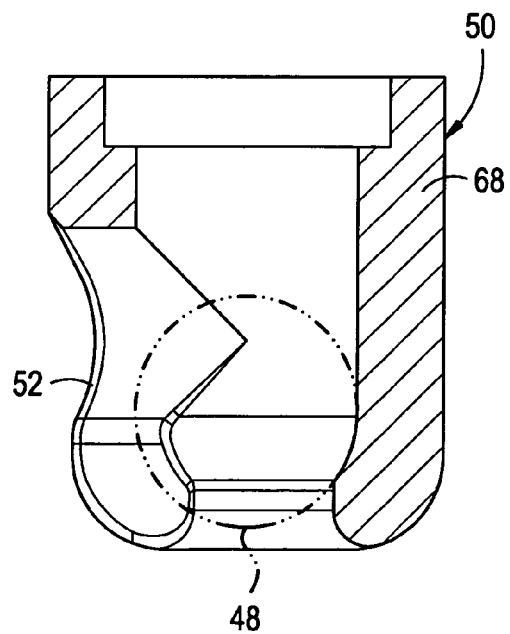
FIG. 9 is a cross-sectional view of one embodiment of a ball joint.

As further shown in FIG. 1, in one embodiment, the articulating implant holder 12 of medical instrument 10 includes a housing 14 having a first end 16 and a second end 18. It should be appreciated that first end 16 and the second end 18 are positioned on opposite and distal ends of the housing 14. A handle 22 is positioned proximate to the first end 16 of the housing 14. It should be appreciated that proximate positioning can encompass positioning that is near, close, adjacent or adjoining. The handle 22 is used by a user to hold the articulating implant holder 12 during a surgical technique. An elongated member 20 is positioned within the housing 14. A knob 28 is attached to the elongated member 20 and is positioned proximate to the first end 16 of the housing 14. A translation mechanism 30 is operatively associated with the first end 16 of the housing and the elongated member 20. A ball joint 50 including a ball 48 (FIG. 2A) and a ball joint housing 68 (FIGS. 8-9) is provided at or proximate to the second end 18 of the housing 14. In one embodiment, the ball joint housing 68 (FIGS. 8-9) is attached to the second end 18 of housing 14 via a threaded connection. However, it should be appreciated that the ball joint 50 and/or ball joint housing 68 can be connected, attached or adapted to operate with the housing 14 using other techniques. Further, in one embodiment, the ball 48 (FIG. 2A) of the ball joint 50 is housed within the ball joint housing 68 (FIGS. 8-9) and the elongated member 20 is adapted to enter the ball joint housing 68 (FIGS. 8-9) to contact the ball 48 (FIG. 2A). A mounting portion 24 is connected to the ball 48 (FIG. 2A) of ball joint 50. The mounting portion 24 includes a collar 58, and the mounting portion 24 is mounted to an implant 26.

Figure 2:
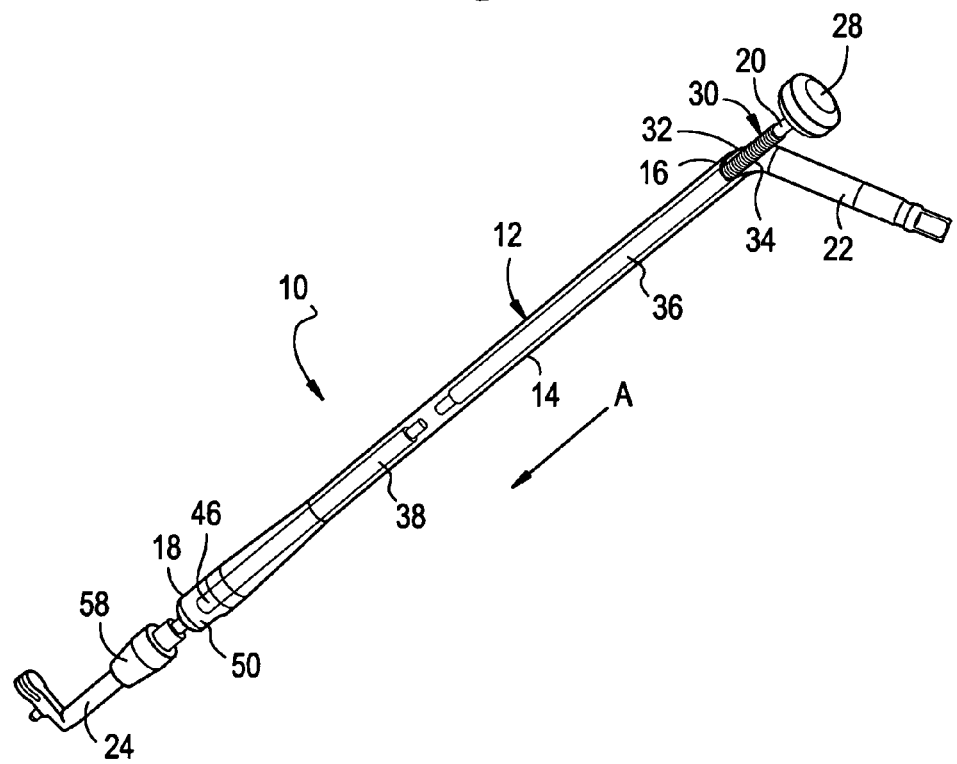
FIG. 2 is a perspective view of one embodiment of a medical instrument.
Figure 2A:
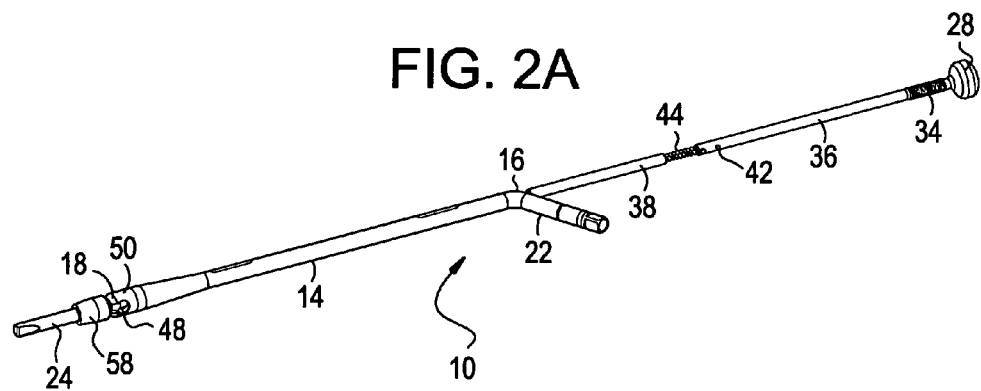
FIG. 2A is a perspective view of one embodiment of a disassembled medical instrument.

As shown in FIG. 2, the elongated member 20 includes an upper member 36 and a lower member 38. In one embodiment, the upper member 36 and the lower member 38 are equal in length. It should be appreciated that, in other embodiment, the upper member 36 and the lower member 38 can have different lengths. The lower member 38 has a formed end 46 that is positioned proximate to the second end 18 of the housing 14. In one embodiment; as shown in FIG. 2, the translation mechanism 30 includes a first threaded portion 32 that is located on an internal portion of the housing 14 at the first end 16 of the housing 14. The upper member 36 of the elongated member 20 includes a second threaded portion 34 located on an exterior surface of the upper member 36. The second threaded portion 34 is located proximate to the knob 28 that is connected to the upper member 36 of the elongated member. The first threaded portion 32 and the second threaded portion 34 are designed to complimentarily and operatively engage or mesh with each other. When the elongated portion 20 is positioned within the housing 14, the first threaded portion 32 and the second threaded portion 34 can be associated and operatively engaged, mated or meshed. When the first threaded portion 32 and the second threaded portion 34 are operatively engaged or meshed together, rotation of the knob 28 causes the upper member 36 of the elongated member 20 to move in a linear direction. Rotation of the knob 28 in a first direction will cause the upper member 36 to move in linear direction A within the housing 14. Rotation of the knob 28 in a direction opposite from the first direction will cause the upper member 36 to move in a linear direction that is opposite from linear direction A within the housing 14. It should be appreciated that movement of the upper member in linear direction A causes the upper member to move in a linear direction extending from and relative to the first end 16 toward the second end 18 of housing 14. Further, movement of the upper member 36 in the linear direction A causes the upper member 36 to move a direction toward the lower member 38. It should further be appreciated that the movement of the upper member 36 in a linear direction can be interpreted as movement in a purely linear direction, and the movement in a linear direction should also be interpreted to encompass movement in a direction that is almost or substantially linear. This almost or substantially linear movement can be envisioned when engagement of the translation mechanism 30 to move the upper member 36 causes the upper member 36 to wobble or vibrate as it moves in the linear direction A.

Figure 6:
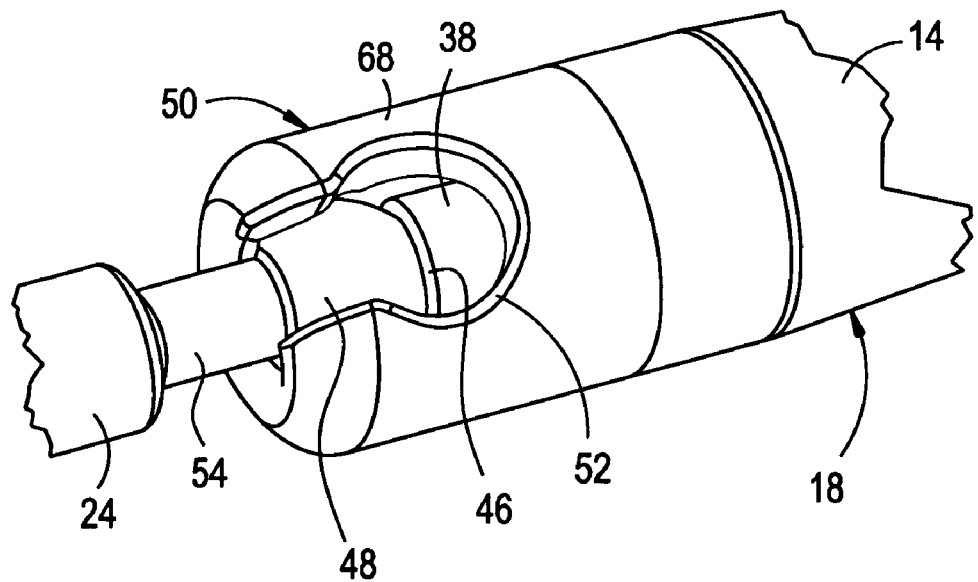
FIG. 6 is a perspective view of one embodiment of a ball joint of a medical instrument.

As shown in FIG. 2A, a biasing member 44 is operatively positioned between the upper member 36 and the lower member 38 of the elongated member 20. When housed within the housing 14 and when the first threaded portion 32 is engaged with the second threaded portion 34, the biasing member 44 supplies or exerts a biasing force to at least the lower member 38. As shown in FIG. 6, the biasing force causes the formed end 46 of the lower member 38 to contact the ball 48 of the ball joint 50 at a given force that is equal to or almost equal to the biasing force. The biasing force-induced contact of the formed end 46 with the ball 48 caused by the biasing force reduces or prevents slop or uncontrolled movement of the mounting portion 24 before the ball 48 is locked to a desired position. In addition, as long as the translation mechanism 30 is engaged, the biasing force will cause the formed end 46 to contact the ball 48. As such, the ball 48 can be moved within the ball joint 50, and thus, the mounting portion 24 and the implant can be moved to a desired position and held in that desired portion by the biasing force before the ball 48 is locked into position in the ball joint 50. In one embodiment, the biasing member 44 comprises a spring. In this embodiment, the biasing force is equal to or proportional to the spring constant of the spring. Further, the biasing force can be predetermined by using a spring having a spring constant that is equal to or proportional to the spring constant of the chosen spring.

As further shown in FIGS. 1-2A, rotation of the knob 28 causes the translation mechanism 30 to move the upper member 36 in linear direction A toward the lower member 38. This movement of the upper member 36 in the linear direction A causes the biasing member 44 to be compressed. The compression of the biasing member 44 causes the biasing force to increases. In one embodiment, the movement of the upper member 36 in the linear direction causes the biasing member 44 to be almost or completely compressed between the upper member 36 and the lower member 38. As mentioned above, this almost or complete compression proportionately increases the biasing force, and as such, a biasing force can be reached that caused the formed end 46 to lock the ball 48 of the ball joint 50. When the ball 48 of the ball joint 50 is locked into position, the mounting portion 24 and implant 26 (when attached) are also correspondingly locked into a position. Further, to allow a user to more easily operate the medical instrument 10 while rotating the knob 28, the user can also hold onto handle 22 during operation, orientation and/or positioning of the implant 26 on the medical instrument 10.

Figure 3:
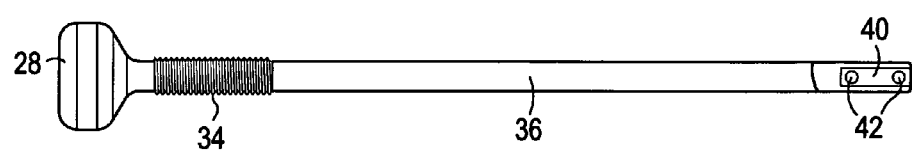
FIG. 3 is a side view of one embodiment of an upper member of an elongated member
Figure 4:
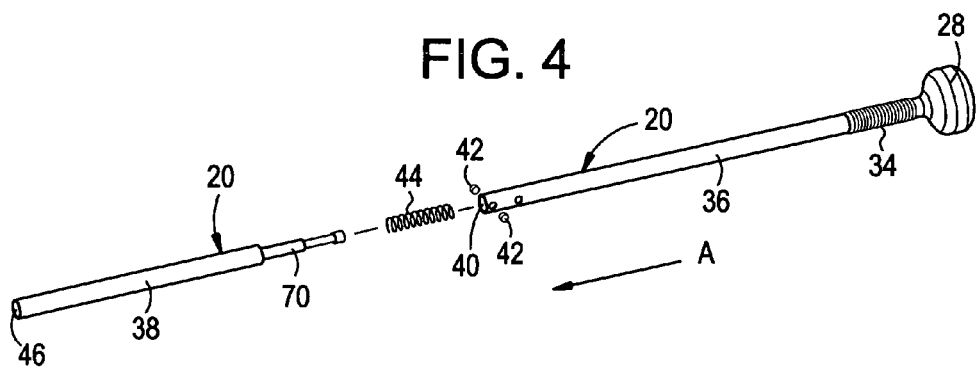
FIG. 4 is a perspective view of one embodiment of an elongated member and a biasing member.
Figure 5:
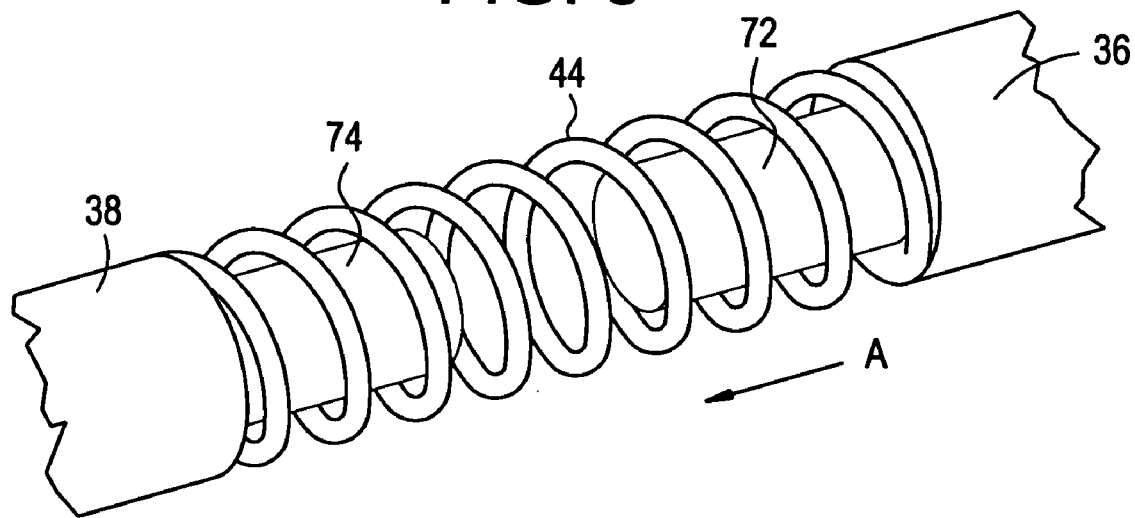
FIG. 5 is a perspective view of one embodiment of an upper member, a lower member and a biasing member.

As shown in FIGS. 3 and 4, in another embodiment, the upper member 36 includes a female portion 40 that is positioned opposite from the knob 28. The lower member 38 also includes a male portion 70 that is positioned opposite from the formed end 46. The female portion 40 is adapted to fit and accept the male portion 70 of the lower member 38. Again, as previously described, the biasing member 44 is positioned between the upper member 36 and the lower member 38. The biasing member 44 is adapted to be positioned over or around the male portion 70 of the lower member 38. One or more pins 42 are positioned in the female portion 40. It should be appreciated that, in one embodiment, the pin 42 can be placed through a wall of the upper member 36 to be positioned in the female portion 40. The pin 42 captures the male portion 70 within the female portion 40 and prevents the male portion 70 from being fully or entirely removed from the female portion 40 because a section of the male portion 70 is adapted to contact the pin 42 preventing such removal. In another embodiment, as the translation mechanism 30 moves the upper member 36 in the linear direction A, the male portion 70 is caused to move further into the female portion 40 as the upper member 36 moves toward the lower member 38. Further, as the upper member 36 moves in the linear direction A the biasing member 44 is compressed and the biasing force increases. In one embodiment, as the upper member 36 moves in the linear direction A, the male portion 70 will move into the female portion 40 such that the upper member 36 makes contact with the lower member 38 before the biasing member is fully compressed. The contact of the upper member 36 with the lower member 38 prevents further movement of the upper member 36 in the linear direction A. Further, the contact of the upper member 36 with the lower member 38 also causes the formed end 46 to lock the ball 48 in the ball joint 50. As discussed above, when the ball 48 of the ball joint 50 is locked into position, the mounting portion 24 and implant 26 (when attached) are also correspondingly locked into a position.

In even another embodiment, the upper member 36 includes upper end 72, and the lower member 38 includes lower end 74. The upper end 72 and the lower end 74 are designed to accept and/or engage the biasing member 44 such that the biasing member 44 is positioned between the upper member 36 and the lower member 38. As the translation mechanism 30 moves the upper member 36 in the linear direction A, the upper end 72 is caused to move closer to the lower end 74. Thus, the upper member 36 is moved closer to the lower member 38. Further, as the upper member 36 moves in the linear direction A, the biasing member 44 is also compressed and the biasing force increases. As the upper member 36 moves in the linear direction A, the upper end 72 will make contact with the lower end 74, and correspondingly the upper member 36 will make contact with the lower member 38. In one embodiment, the upper member 36 will make contact with the lower member 38 before the biasing member is fully compressed. The contact of the upper member 36 with the lower member 38 prevents further movement of the upper member 36 in the linear direction A. Further, the contact of the upper member 36 with the lower member 38 also causes the formed end 46 to lock the ball 48 in the ball joint 50. Again, as discussed above, when the ball 48 of the ball joint 50 is locked into position, the mounting portion 24 and implant 26 (when attached) are also correspondingly locked into a position.

Figure 10:
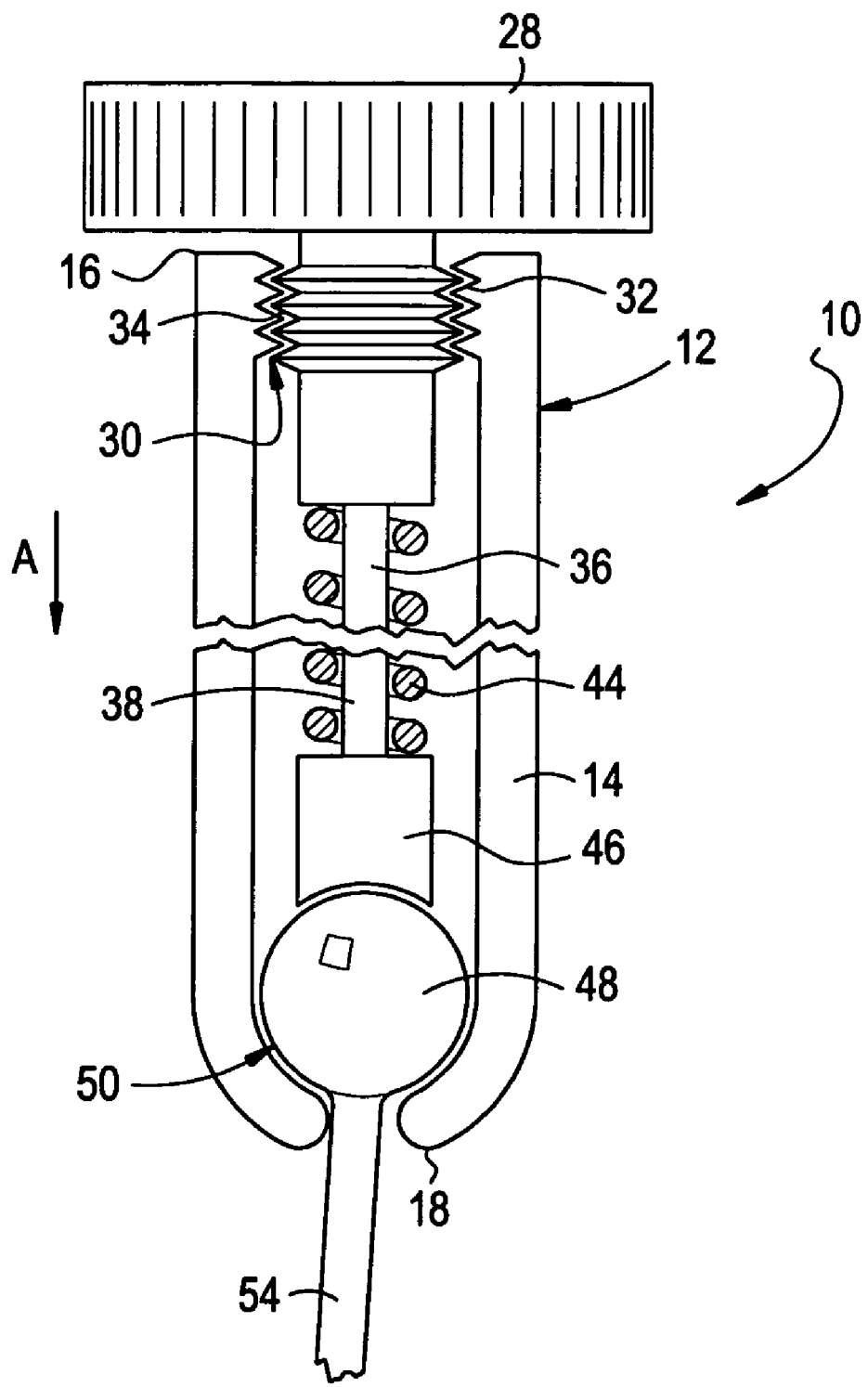
FIG. 10 is a partial cross-sectional view of one embodiment of a medical instrument.

As shown in FIG. 6, the ball joint 50 is positioned at and/or connected to the second end 18 of the housing 14. As previously discussed, the ball joint 50 includes a ball 48 housed within a ball joint housing 68. The ball 48 is connected to the mounting portion 24. In one embodiment, the ball 48 is connected to mounting portion 24 via neck 54. In another embodiment, the ball joint housing 68 includes a key slot 52. As further shown in FIG. 6, the formed end 46 is caused to contact the ball 48 via the biasing force. Also, the formed end 46 is caused to lock the ball 48 into the ball joint 50 as described hereinabove. In addition, as further shown in FIG. 6 and FIG. 10, the formed end can comprise a cupped shape that is adapted to accept and/or hold the ball 48 of the ball joint 50.

Figure 7:
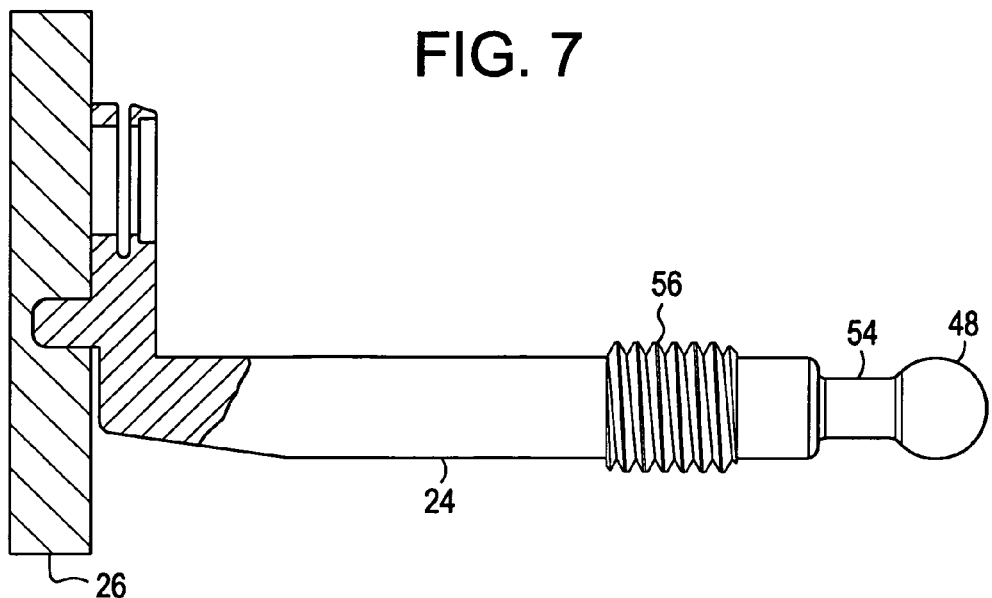
FIG. 7 is a side view and partial cross-sectional view of a mounting portion and ball.

In FIG. 7, the mounting portion 24 is releasably connected to and/or releasable holds an implant 26. It should be appreciated that, in one embodiment, the mounting portion 24 can be mounted to the implant 26 using a threaded connection, a snap-on connection, magnetic connection or other connection mechanisms. Further, it should also be appreciated that the implant 26 can comprise a various surgical implants, such as, a rod, screw, plate or other surgical implants used in various surgical procedures, such as, a spinal surgical procedure. Further, the mounting portion 24 also includes collar threads 56 wherein collar 58 (FIGS. 1 and 2) is attached to the mounting portion 24. It should be appreciated that the collar 58 (FIGS. 1 and 2) could be attached to the mounting portion 24 using attachment mechanisms other than threads. In addition, the collar 58 (FIGS. 1 and 2) can be used as another mechanism to lock the ball joint 50 in a desired position or further limit movement of the ball joint 50.

As shown in FIGS. 6-9, the ball 48 is connected to the mounting portion 24 via neck 54. The ball joint 50 further includes a key slot 52 in the ball joint housing 68. The neck 54 can be positioned within the key slot 52 such that the mounting portion 24 can be positioned into a desired position during a medical procedure. It should be appreciated that the use of key slot 52 can allow for more desired positions than other embodiments without a key slot 52.

Figure 11:
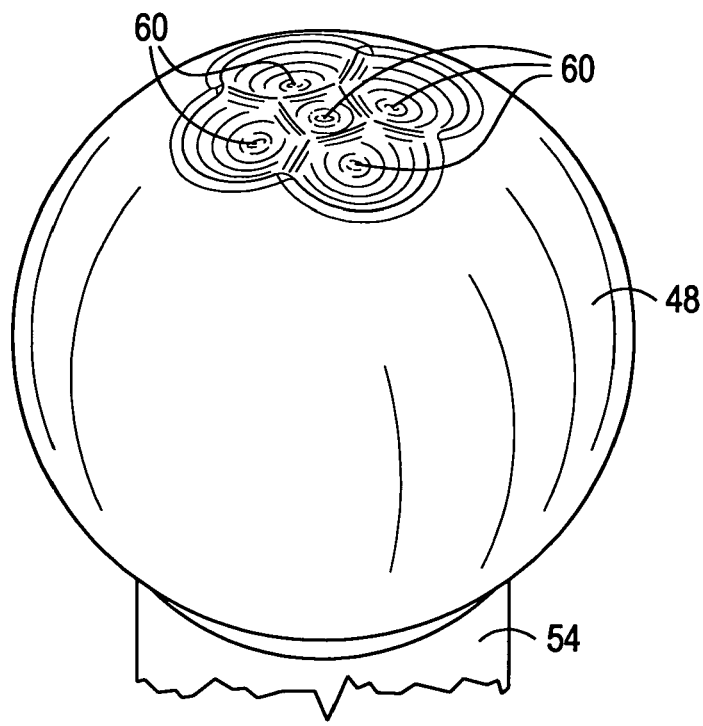
FIG. 11 is a perspective view of one embodiment of a ball of a ball joint.
Figure 12:
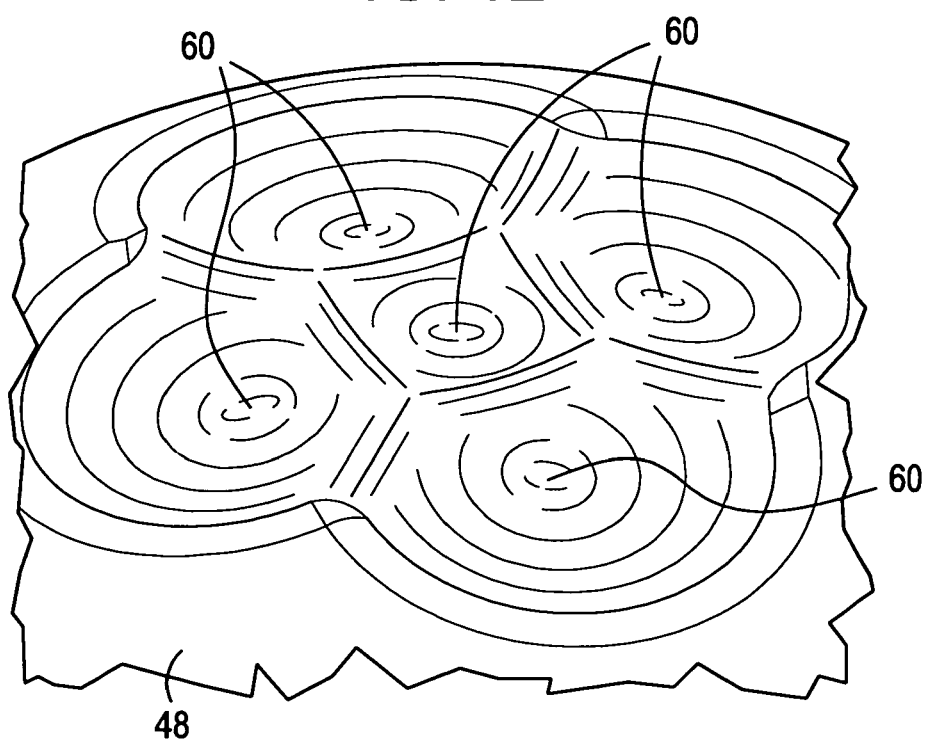
FIG. 12 is a magnified view of one embodiment of a portion of a ball of a ball joint.
Figure 13:
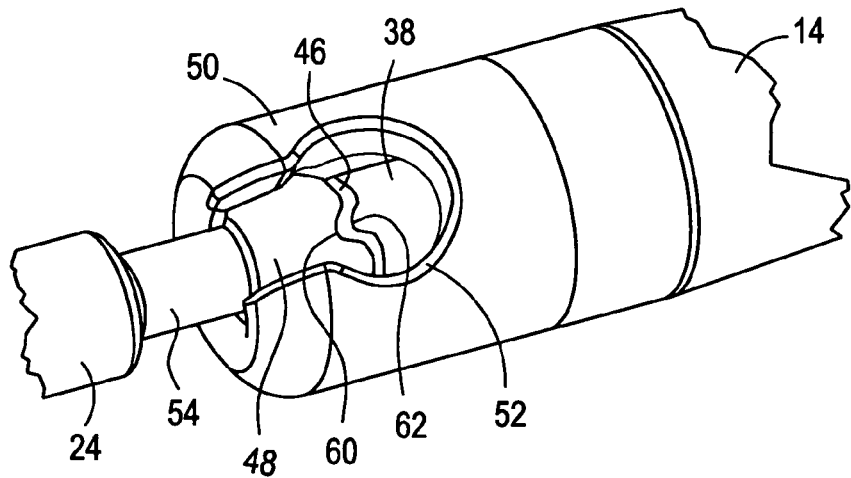
FIG. 13 is a perspective view of another embodiment of a ball joint of a medical instrument.
Figure 14:
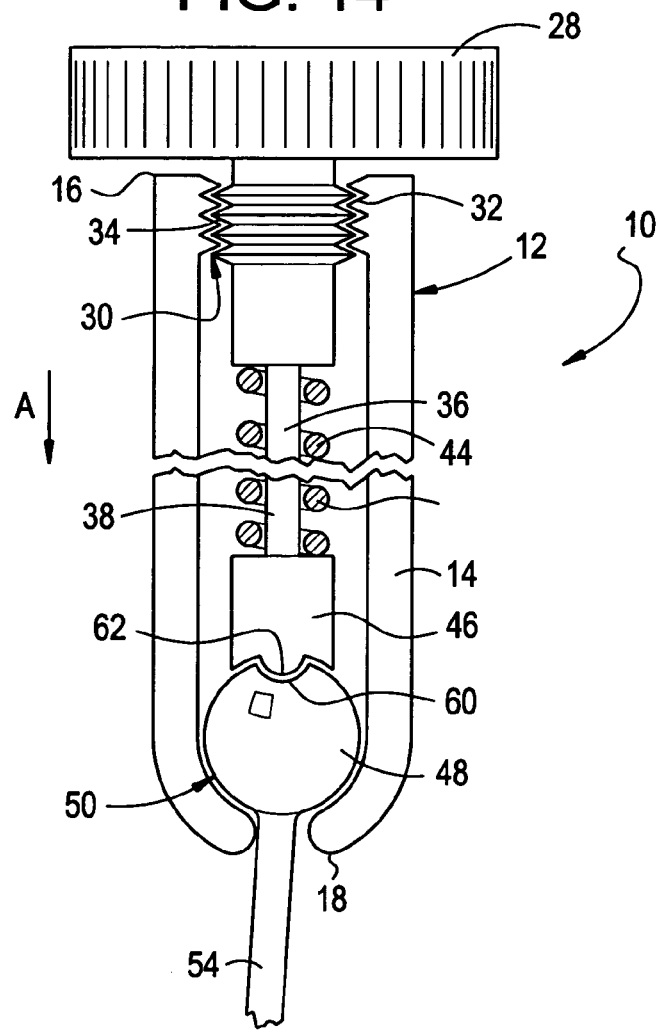
FIG. 14 is a partial cross-sectional view of another embodiment of a medical instrument.

As further shown in FIGS. 11 and 12, in another embodiment, the ball 28 of ball joint 50 includes one or more recess 60. The recess 60 corresponds to a desired position that the implant 26 can be positioned during a medical procedure. As further shown in FIGS. 13 and 14, in even another embodiment, the formed end 46 includes a detent 62 that is adapted to mate with the recess 60. As such, the detent 62 allows the formed end 46 to easily mate with the recess 60 of the ball 48 such that the implant 26 can more easily be positioned in a desired position or orientation. In addition, the biasing member 44 will exert a biasing force that ultimately causes the detent 62 of the formed end 46 to be seated in the recess 60 of the ball 48. As further described above, further movement of the translation mechanism 20 can cause the formed end 46 to lock the ball 48 into the ball joint 50 and thus cause the implant 26 to be positioned in a desired position during medical procedure.

Figure 15:
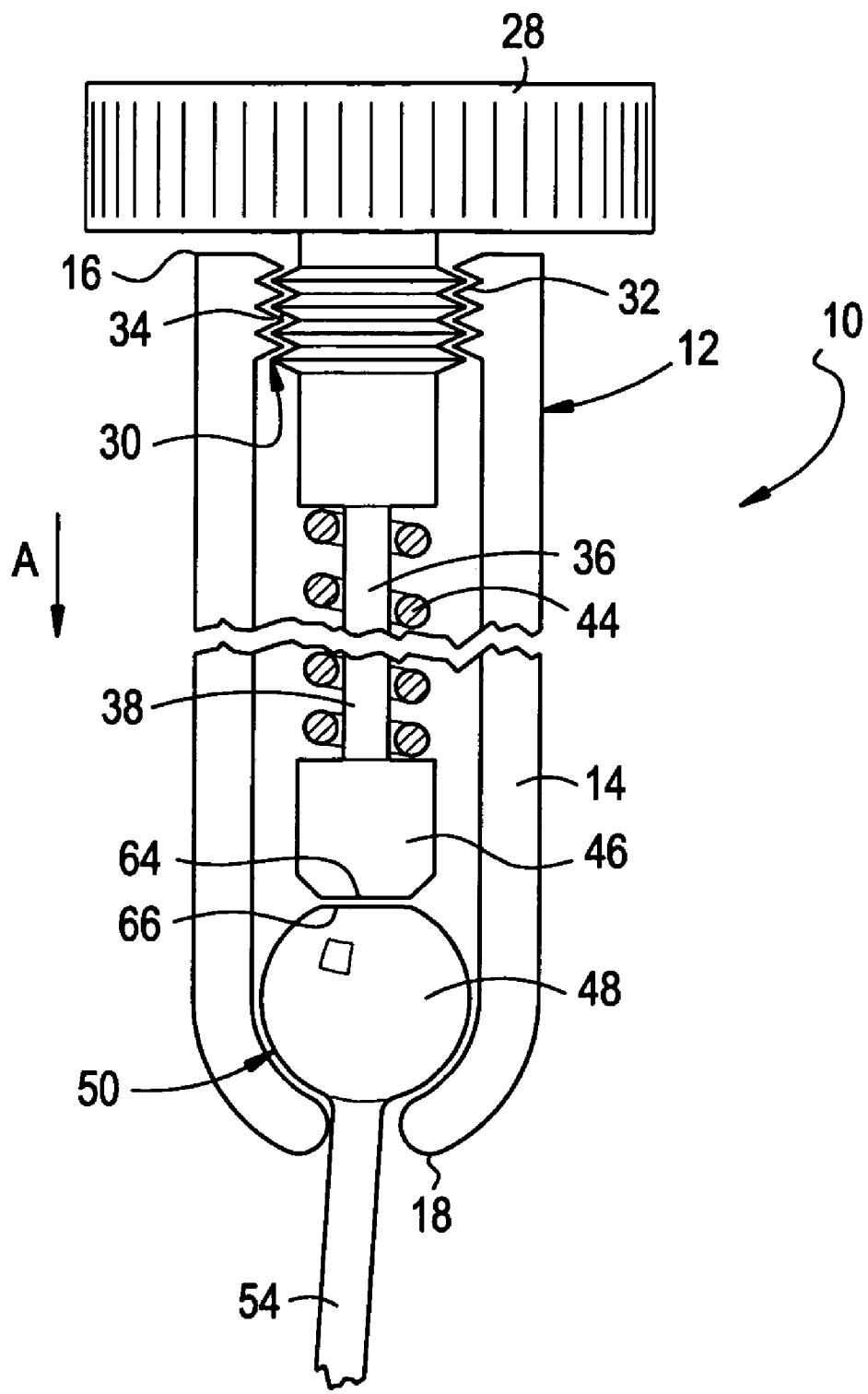
FIG. 15 is a partial cross-sectional view of yet another embodiment of a medical instrument.

As also shown in FIG. 15, in yet another embodiment, the ball 28 of ball joint 50 includes one or more flat 66. The flat 66 corresponds to a desired position that the implant 26 can be positioned during a medical procedure. As further shown, the formed end 46 also includes a flat end 64 that is adapted to mate with the flat 66. As such, the flat end 64 allows the formed end 46 to easily mate with the flat 66 of the ball 48 such that the implant 26 can more easily be positioned in a desired position or orientation. In addition, the biasing member 44 will exert a biasing force that ultimately causes the flat end 64 of the formed end 46 to be mated with the flat 66 of the ball 48. As further described above, further movement of the translation mechanism 20 can cause the formed end 46 to lock the ball 48 into the ball joint 50 and thus cause the implant 26 to be positioned in a desired position during medical procedure.

In even another embodiment, a surgical method for using the medical instrument 10 is provided. The surgical method includes providing a medical instrument 10 for use during the medical procedure, such as, a surgical procedure including, for example, a spinal surgical procedure. The implant 26 is releasably attached to the medical instrument 10 using mounting portion 24. As discussed above, the mounting portion 24 can be attached to the implant 26 using a threaded connection, a snap-on connection, magnetic connection or other connection mechanisms. During the surgical procedure, access is provided to an implantation area of a surgical site. In one embodiment, a surgeon creates a surgical site by making an incision in a patient. Further, the surgical site can be created using minimal access surgical techniques, a percutaneous surgical technique, an open surgical technique, a mini-open surgical technique, other surgical techniques or any combination of various surgical techniques. In this regard, the incision is further opened to provide access to the implantation area. In another embodiment, the implantation area is one or more vertebral bodies in the spinal column of the patient. The implant 26 is locked in a desired position on the medical instrument 10. In one embodiment, the implant 26 is locked by rotation of the knob 28 that causes the translation mechanism 30 to move the upper member 36 to move toward the lower member 38 of the elongated member 20. The biasing member 44 placed between the upper member 36 and the lower member 38 is compressed as the upper member 36 is moved toward the lower member 38. As the biasing member 44 is compressed, the biasing force applied to the lower member 38 is increased. The biasing force is also translated to the formed end 46 of the lower member 38 causing the formed end 46 to contact the ball 48 of the ball joint 50. Thus, the force of the formed end 46 against the ball 48 also increases as the upper member 36 moves toward the lower member 38. In one embodiment, as the upper member 36 is further moved toward the lower member 38, a biasing force from the biasing member 44 causes a force between formed end 46 and the ball 48 such that the ball 48 is locked into the ball joint 50, and thus, the mounting portion 24 and any attached implant 26 are also locked into a desired position. In another embodiment, as the upper member 36 is further moved toward the lower member 38, the upper member 36 is caused to contact the lower member 38 such that the ball 48 is locked into the ball joint 50, and thus, the mounting portion 24 and any attached implant 26 are also locked into a desired position. As discussed above, it should further be appreciated that the biasing member 44 provides a force to be applied between the formed end 46 and the ball 48 such that the mounting portion 24 that is attached to the ball 48 can be oriented to a desired position and held in that position via the force before the ball 48 is locked into position via one of the embodiments discussed hereinabove. Before or after the implant 26 is locked to the medical instrument 10, the medical instrument 10 is inserted into the patient at the surgical site. The medical instrument 10 is maneuvered in the surgical site such that the implant 26 is positioned to the implantation area. The implant 26 is attached to the patient at the implantation area. In addition, it should be appreciated that before, after or during implantation of the implant 26 into the patient, the medical instrument 10 via the handle 22 can be oriented or manipulated relative to the implant 26 to improve visibility or access to the implant 26 during the medical procedure. In one embodiment, the implant 26 comprises a spinal plate, and the spinal plate is attached to at least one vertebral body of the spinal column of the patient. The implant 26 is detached from the medical instrument 10 and the medical instrument is removed from the surgical site of the patient.

The foregoing discussion of the invention has been presented for purposes of illustration and description. Further, the description is not intended to limit the invention to the form disclosed herein. Consequently, variations and modifications commensurate with the above teachings and with the skill and knowledge of the relevant art are within the scope of the present invention. The embodiment described herein above is further intended to explain the best mode presently known of practicing the invention and to enable others skilled in the art to utilize the invention as such, or in other embodiments, and with the various modifications required by their particular application or uses of the invention. It is intended that the appended claims be construed to include alternative embodiments to the extent permitted by the prior art.

What is claimed is:

1. An apparatus for holding and orienting an implant during a medical procedure, said apparatus comprising:
   a housing having a first end and a second end;
   an elongated member disposed within said housing, said elongated member comprising an upper member and a lower member, said lower member having a formed end positioned proximate to said second end of said housing;
   a biasing member operatively positioned between said upper member and said lower member and at least partially wrapped around at least a portion of said upper member and said lower member, said biasing member adapted to supply a biasing force to at least said lower member;
   a ball joint comprising a ball housed within a ball joint housing positioned at said second end of said housing;
   a mounting portion connected to said ball and releasably attachable to the implant; and
   a translation mechanism operatively associated with said first end of said housing and said upper member, wherein said biasing force normally biases said formed end of said lower member in contact with said ball while permitting said ball to be moved to a first desired position and held in said first desired position with said biasing force, said translation mechanism adapted to move said upper member in at least a first linear direction toward said lower member causing said formed end of said lower member to lock said ball of said ball joint whereby locking said ball joint and orienting said implant in at least said first desired position.

2. The apparatus of claim 1 wherein said translation mechanism comprises a first threaded portion connected to said first end of said housing and a second threaded portion connected to said upper member wherein said first threaded portion and said second threaded portion operatively and correspondingly mate to move said upper member in at least said first linear direction.

3. The apparatus of claim 2 wherein said upper member further comprises a knob positioned proximate to said first end of said housing.

4. The apparatus of claim 3 wherein rotation of said knob causes said first threaded portion to correspondingly mesh with said second threaded portion and move said upper member in at least said first linear direction.

5. The apparatus of claim 1 further comprising a handle connected to said housing and positioned proximate to said first end of said housing.

6. The apparatus of claim 1 wherein said lower member further comprises a male portion, said male portion positioned opposite from said formed end.

7. The apparatus of claim 6 wherein said upper member further comprises a female portion positioned to accept said male portion of said lower member.

8. The apparatus of claim 7 wherein said upper member further comprises at least one pin positioned in said female portion, said pin capturing said male portion of said lower member into said female portion of said upper member and preventing said male portion of said lower member from being entirely removed from said female portion of said upper member.

9. The apparatus of claim 7 wherein movement of said upper member in at least said first linear direction moves said male portion of said lower member further into said female portion of said upper member whereby causing said upper member to contact said lower member preventing further movement of said upper member in at least said first linear direction.

10. The apparatus of claim 9 wherein said upper member contacts said lower member preventing further movement of said upper member in at least said first linear direction before said biasing member is fully compressed.

11. The apparatus of claim 1 wherein when said upper member contacts said lower member further movement of said upper member is prevented in at least said first linear direction before said biasing member is fully compressed.

12. The apparatus of claim 1 wherein said biasing member comprises a spring.

13. The apparatus of claim 1 wherein said formed end comprises a cupped shape adapted to accept said ball of said ball joint.

14. The apparatus of claim 1 wherein said formed end comprises a detent and said ball further comprises a recess adapted to mate with said detent, wherein said recess corresponds to a desired portion of said implant.

15. The apparatus of claim 14 wherein said ball further comprises a plurality of recesses, wherein each of said plurality of recesses corresponds to a desired position.

16. The apparatus of claim 1 wherein said formed end comprises a flat end and said ball further comprises a flat adapted to mate with said flat end, wherein said flat corresponds to a desired position of said implant.

17. An apparatus for holding and orienting an implant during a medical procedure, said apparatus comprising:
    an elongated member comprising an upper member and a lower member, said lower member having a formed end;
    a biasing member operatively positioned between said upper member and said lower member and at least partially wrapped around at least a portion of said upper member and said lower member, said biasing member adapted to supply a biasing force to at least said lower member;
    a ball joint comprising a ball, said ball joint positioned and adapted to accept said formed end of said lower member, said biasing force causing said formed end of said lower member to contact said ball; and
    a translation mechanism adapted to move said upper member in at least a first linear direction toward said lower member, wherein said biasing force normally biases said formed end of said lower member in contact with said ball while permitting said ball to be moved to a first desired position and held in said first desired position with said biasing force, and movement of said translation mechanism in said first linear direction causes said formed end of said lower member to lock said ball of said ball joint whereby locking said ball joint and orienting said ball of said ball joint in at least said first desired position.

18. The apparatus of claim 17 wherein when said upper member contacts said lower member further movement of said upper member is prevented in at least said first linear direction before said biasing member is fully compressed.

19. The apparatus of claim 17 wherein said biasing member comprises a spring.

20. The apparatus of claim 17 wherein said formed end comprises a cupped shape adapted to accept said ball of said ball joint.

21. The apparatus of claim 17 wherein said formed end comprises a detent and said ball further comprises a recess adapted to mate with said detent, wherein said recess corresponds to a desired portion of said implant.

22. The apparatus of claim 21 wherein said ball comprises a plurality of recesses, wherein each of said plurality of recesses corresponds to a desired position.

23. A surgical method comprising:
providing a medical instrument comprising:
an elongated member comprising an upper member and a lower member, said lower member having a formed end;
a biasing member operatively positioned between said upper member and said lower member, said biasing member adapted to supply a biasing force to at least said lower member;
a ball joint comprising a ball, said ball joint positioned and adapted to accept said formed end of said lower member; and
a translation mechanism adapted to move said upper member in at least a first linear direction toward said lower member, wherein said biasing force normally biases said formed end of said lower member in contact with said ball while permitting said ball to be moved to a first desired position and held in said first desired position with said biasing force, and movement of said translation mechanism in said first linear direction causes said formed end of said lower member to lock said ball of said ball joint whereby locking said ball joint and orienting said ball of said ball joint in at least a first desired position;
releasably attaching an implant to said medical instrument;
providing access to an implantation area of a surgical site in a patient;
orienting and locking said implant to said medical instrument in at least one said first desired portion;
inserting said medical instrument into said surgical site in said patient;
positioning said medical instrument in said surgical site whereby said implant is positioned to said implantation area;
attaching said implant to said patient at said implantation area;
detaching said implant from said medical instrument; and
removing said medical instrument from said surgical site of said patient.

* * * * *